(12) United States Patent
Mishra et al.

(10) Patent No.: US 7,651,507 B2
(45) Date of Patent: Jan. 26, 2010

(54) TISSUE PROCESSING SYSTEM

(75) Inventors: Ajit Mishra, San Antonio, TX (US);
Charles Seegert, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 552 days.

(21) Appl. No.: 10/379,342

(22) Filed: Mar. 3, 2003

(65) Prior Publication Data

US 2004/0176787 A1    Sep. 9, 2004

(51) Int. Cl.
*A61B 17/50* (2006.01)
(52) U.S. Cl. .................................... 606/131
(58) Field of Classification Search ......... 606/131–133, 606/9, 6, 10
See application file for complete search history.

(56) References Cited

U.S. PATENT DOCUMENTS

| | | | |
|---|---|---|---|
| 3,076,462 A | 2/1963 | Meek et al. | |
| 3,613,242 A * | 10/1971 | Hill et al. | 606/132 |
| 3,640,279 A | 2/1972 | Brown et al. | |
| 4,773,418 A | 9/1988 | Hettich | |
| 5,152,757 A | 10/1992 | Eriksson | 604/305 |
| 5,196,020 A | 3/1993 | Atkinson et al. | |
| 5,423,778 A | 6/1995 | Eriksson et al. | 604/305 |
| 6,063,094 A | 5/2000 | Rosenberg | |
| 6,248,114 B1 * | 6/2001 | Ysebaert | 606/132 |

FOREIGN PATENT DOCUMENTS

| | | |
|---|---|---|
| FR | 1 497 723 A | 10/1967 |
| JP | 60-500279 | 3/1985 |
| JP | 2000-501311 | 2/2000 |
| JP | 2001-507584 | 6/2001 |
| JP | 2006-519071 | 8/2006 |
| WO | WO 01/27586 | 4/2001 |
| WO | WO 2004/075764 A | 9/2004 |

OTHER PUBLICATIONS

Andree et al., "In vivo transfer and expression of a human epidermal growth factor gene accelerates wound repair," *Proc Natl Acad Sci U S A.*, 91:12188-12192, 1994.
Breuing et al., "Healing of partial thickness porcine skin wounds in a liquid environment," *J. of Surgical Research*, 52:50-8, 1992.
Eriksson et al., "In vivo gene transfer to skin and wound by microseeding," *Journal of Surgical Research*, 78:85-91, 1998.
Eriksson et al., "Treatment of chronic, nonhealing abdominal wound in a liquid environment," *Annals of Plastic Surgery*, 36:80-83, 1996.

(Continued)

*Primary Examiner*—Kevin T Truong

(57) ABSTRACT

A tissue processing system includes a series of blades arranged in parallel to form a tissue processor. The blades may be adjusted to create a spaced between each blade in the range of 250-1000 microns. A slicer is included to remove a donor tissue to be processed by the processor. The processor is rotatable 90 degrees so as to create uniform micrografts of tissue for transplanting to a recipient site. An extractor is included to remove tissue particles from the processor after they have been cut into an appropriate size. A cutting block may be provided to ensure uniform thickness of cuts of the donor tissue.

19 Claims, 2 Drawing Sheets

OTHER PUBLICATIONS

Gallo et al., "Syndecans, cell surface heparan sulfate proteoglycans, are induced by a proline-rich antimicrobial peptide from wounds," *Proc Natl Acad Sci U S A*, 91:11035-11039, 1994.

Marikovsky et al., "Wound fluid-derived herapin-binding EGF-like growth factor (HB-EGF) is synergistic with insulin-like growth factor-I for balb/Mk keratinocyte proliferation," *The Journal of Investigative Dermatology*, 106:616-621, 1996.

Pomahac et al., "Tissue engineering of skin," *Crit. Rev. Oral Biol. Med.*, 9(3):333-344, 1998.

Svensjö et al., "Accelerated healing of full-thickness skin wounds in a wet environment," *Plastic and Reconstructive Surgery*, 106(3):602-612, 2000.

Svensjö et al., "Healing of full-thickness porcine wounds in dry, moist, and wet environments," *Surgical Forum*, 48:691-693, 1997.

Vogt et al., "Dry, moist, and wet skin wound repair," *Annals of Plastic Surgery*, 34:493-500, 1995.

Vogt et al., "Genetically modified keratinocytes transplanted to wounds reconstitutes the epidermis," *Proc Natl Acad Sci U S A*, 91:9307-9311, 1994.

Yao et al., "Tetracycline repressor, tetR, rather than the tetR-mammalian cell transcription factor fusion derivatives, regulates inducible gene expression in mammalian cells," *Human Gene Therapy*, 9:1939-1950, 1998.

Office Communication, issued in Japanese Patent Application No. JP 2006-508950, issued Sep. 8, 2009.

Office Communication, issued in Mexican Patent Application No. PA/a/2004/011827, issued Sep. 2, 2009.

* cited by examiner

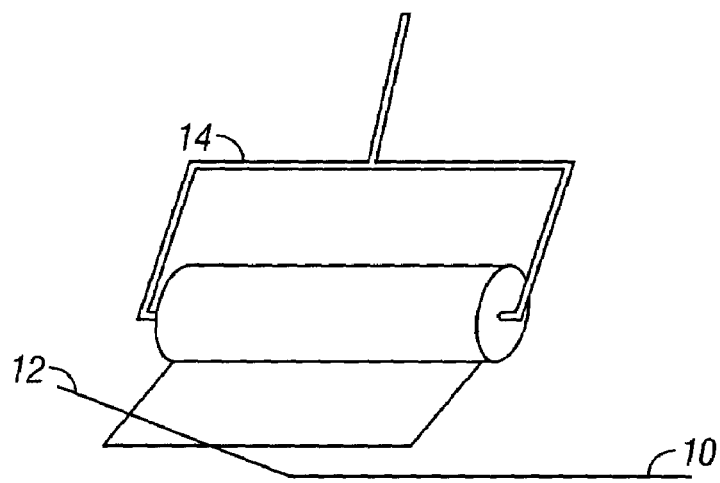
FIG. 1
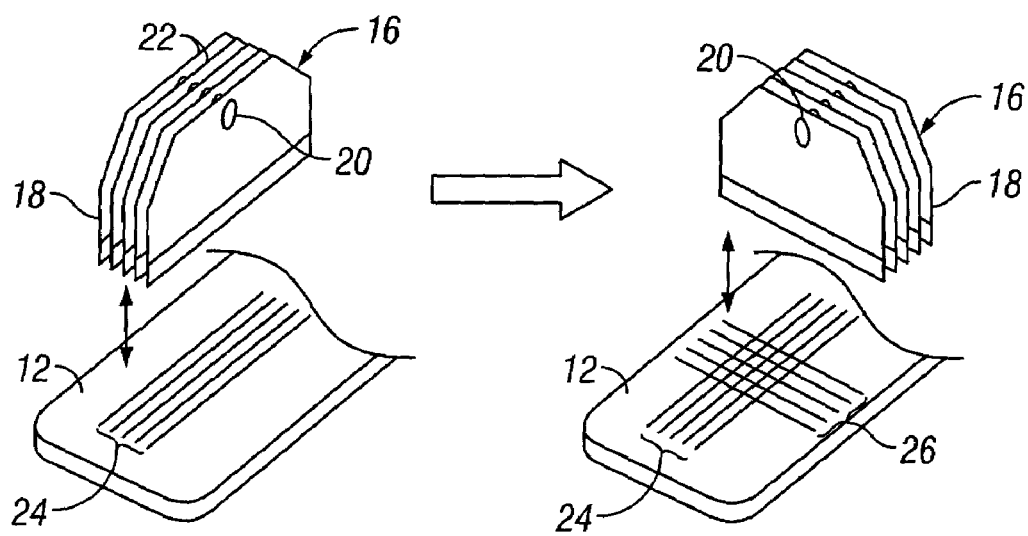
FIG. 2A  FIG. 2B
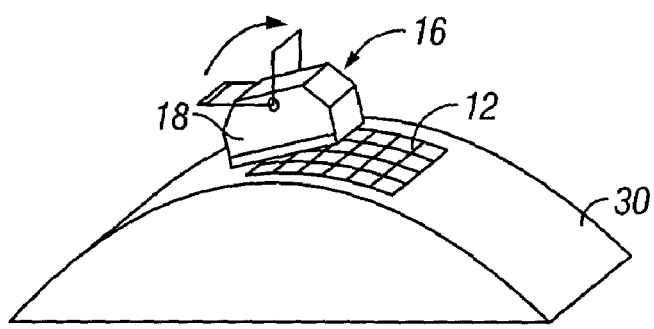
FIG. 3

TISSUE PROCESSING SYSTEM

FIELD OF THE INVENTION

The invention relates to a system for processing dermal tissue. More particularly, this invention relates to a system for extracting and processing dermal tissue into small particles for purposes of transplantation to a recipient site.

BACKGROUND OF THE INVENTION

Traditional skin grafting is accomplished by taking a thin slice of dermal tissue from a donor site in order to cover a wound site, such as a bum area. In some instances, the slice of dermal tissue is meshed to expand its size, creating a meshed graft. Traditional devices used to harvest the tissue from the donor site include dermatomes for removing a thin slice of the upper layers of skin from a donor site. The slice is then meshed using traditional techniques to create and expand the sheet of skin tissue, that gives the slice a weave-like appearance. The purpose of expanding the skin from the donor site is to increase the amount of area on a recipient site that can be covered by the donor site. Some of the most desirable expansion ratios currently available are 6:1. That is, under the most ideal conditions, skin taken from a donor site would be able to cover a recipient site that is six times larger than the donor site.

Traditional meshed grafting techniques have been shown to yield 90% viability at the donor site. A slightly lower viability rate occurs for non-meshed sheet grafts, mostly due to fluid accumulation under the sheet graft. Factors that lead to graft failure include poor circulation, unclean wounds, patient interference with the graft dressing, obesity, and smoking. Additionally, in at least approximately 10% of cases, infection at the donor site occurs. Although such donor site infections are not likely related to graft failure at the wound site, they still pose problems for both the patient and caregiver.

As mentioned, traditional meshing techniques yield a most favorable expansion ratio of 6:1. For example, a 1 $cm^2$ donor site can cover a 6 $cm^2$ wound site. While greater ratios of 9:1 and 12:1 may be possible using meshing techniques, there is also a significant delay in epithelialization with such ratios.

Micro grafting techniques, in which the donor tissue is actually minced in order to achieve a greater than 10:1 expansion ratio, are known in the art. Such techniques allow for a much greater coverage area from a small donor site. However, traditional techniques are cumbersome, and often the viability of the cells is compromised to such an extent that sometimes less than 50% of the cells are viable when applied to the wound site. Additionally, traditional techniques have thus far been inadequate in producing viable cells in the range of 250 microns, 500 microns and 1000 microns.

It is therefore an object of this invention to provide a system for obtaining and processing tissue samples from a donor site on the order of 250-1000 microns in size, such that the vast majority of tissue processed at this size is viable when transplanted to a recipient site.

Additional objects of the present invention include a significant reduction in the size of the donor site as compared to traditional mesh-graft procedures; minimizing scarring of the graft site as compared to traditional mesh-graft procedures; improvement of the pliability of tissue in the graft site; improvement of the cosmetic appearance of the graft site as compared to current methods; and improvement of graft "take."

SUMMARY OF THE INVENTION

In accordance with the foregoing objects, the present invention generally comprises a device for obtaining tissue from a donor site, a tissue processor for processing the tissue into particles in the size range of 250-1000 microns, and a means for releasing the processed cells from after they have been processed into the desired size range.

The present invention includes a tissue slicer for removing a tissue sample from a donor site. The typical donor site may be equivalent to a split—thickness—skin graft ("STSG"). The tissue slicer may be incorporated into the tissue processor as a single unit, or alternatively, may be a separate unit, such as a traditional dermatome. A tissue processor consists of a series of sharpened blades arranged parallel to one another, and maneuvered over the STSG in two passes, wherein each pass is at a ninety degree angle to the first pass. Alternatively, multiple sets of processors are arranged perpendicular to one another in a single tissue processor, such that the tissue is processed in one step by the use, and in which the tissues are cut to the appropriate size in one pass. A curved cutting surface may also be provided to ensure that even pressure is applied across the surface of the STSG so that uniform tissue particles are produced.

The present invention also includes a tissue extractor for removing the tissue samples after the tissue processor has processed them. The size range of the tissue processed may result in the processed tissue becoming trapped within the confines of the processor, such as between the parallel-arranged blades. The extractor consists of a series of wires interspersed between the blades, and positioned below the cutting surface of the blades. The wires are extended to a handle at their distal end, and hinged at their proximal end. After processing, the wires can be pulled from between the blades by the handle, which in turn grasps the processed tissue. The processed tissue is then captured by the extractor for easy removal, such as by flushing the extractor, or wiping the extractor.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which:

FIG. 1 is a perspective view of a tissue slicer, illustrating the manner in which a split-thickness-skin graft may be obtained.

FIGS. 2A and 2B are perspective views generally illustrating the tissue processor assembly of the present invention.

FIG. 3 is a perspective view of the tissue processor in use with the curved cutting surface of the present invention.

DESCRIPTION OF THE INVENTION

Figure 4A:
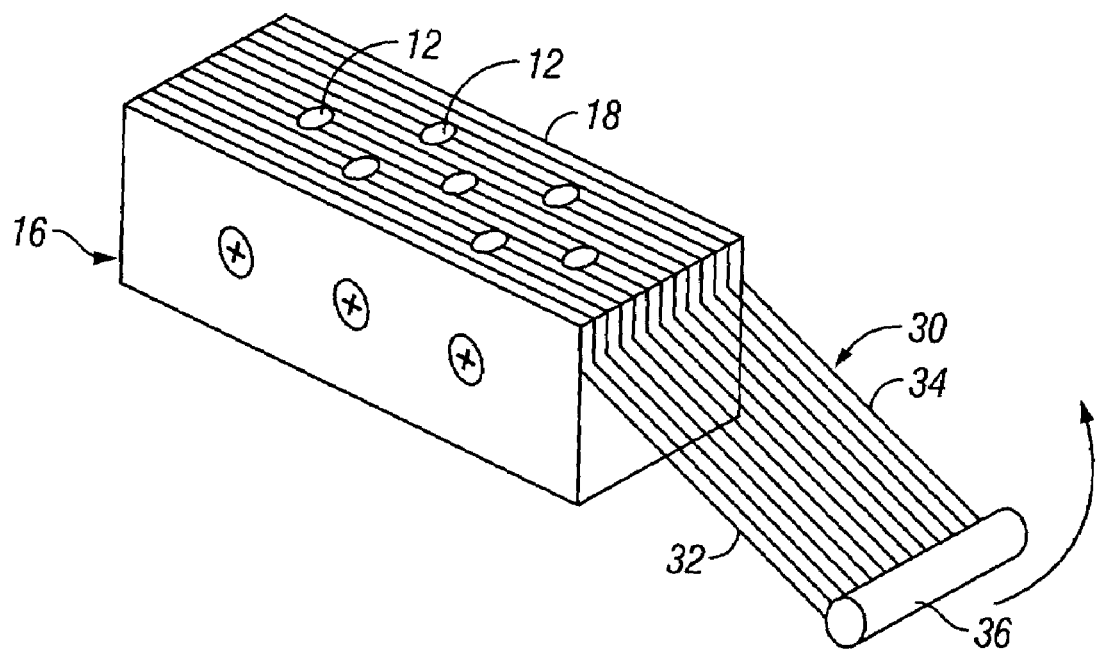
FIGS. 4A and 4B are perspective representations of the tissue extractor of the present invention.

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

Referring now to the drawings, the details of preferred embodiments of the present invention are graphically and schematically illustrated. Like elements in the drawings are represented by like numbers, and any similar elements are represented by like numbers with a different lower case letter suffix.

As illustrated in FIG. 1, a donor tissue sample 12, such as a split-thickness-skin graft ("STSG") may be removed from a healthy region of skin tissue 10 using a traditional tissue slicer, such as a dermatome 14, which may be incorporated into the present invention in a single unit device, or alternatively, a traditional dermatome may be utilized to obtain a STSG, and the present invention utilized to process the donor tissue.

After the donor tissue is removed from the donor site, the tissue is processed by the tissue processor 16, as illustrated in FIGS. 2A and 2B. In an alternative embodiment, the tissue processor 16 cuts the donor tissue at the donor site 10 directly. The tissue processor is comprised of a series of sharpened blades 18 arranged in parallel to one another and fixed along an axis 20. The distance 22 between the blades 18 may be adjusted according to the desired size of the tissue sample to be obtained. The preferred distance 22 between each blade 18 is in the range of about 250 microns to 1000 microns. The most preferable distance 22 is one of about 250 microns, 500 microns, or 1000 microns. In the preferred embodiment, the blades 18 may be adjusted to one of the three most preferred distances mentioned. Alternatively, the distance 22 between the blades 18 of the processor 16 are fixed to one of the three most preferable distances mentioned. In still another alternative embodiment, the distance 18 may be adjustable to any measurement within the preferred range of 250-1000 microns. The distance 22 between the blades 18 allows for uniform tissue particles to be produced at the ideal range of 250 square microns to 1000 square microns. Tissue particles within the desired range have been shown to yield the highest expansion ratio while retaining the greatest viability.

In the preferred embodiment, two sets of cuts are made into the donor tissue 12. The first cut, as illustrated in FIG. 2A, create a first series of parallel cuts 24 through the donor tissue 12 when the processor is depressed into the tissue 12. The second cut, as illustrated in FIG. 2B, create a second series of parallel cuts 26 that are in perpendicular arrangement to first cuts 24. In use, the first set of cuts 24 are made by the user, who subsequently turns the processor 16 to an angle about 90 degrees from the first set of cuts 24 to make the second set of cuts 26. Alternatively, the processor 16 may be automated to make the first set of cuts during a first pass of the processor across the donor tissue 12, and the processor 16 is automatically rotated 90 degrees prior to a second pass of the processor 16 across the surface of the tissue 12. An electronic motor (not shown) as known in the art may be utilized for automated rotation of the processor 16. In such an embodiment, a switch (also not shown) may be integrated with the motor, wherein the switch is activated as the processor 16 changes direction. Each change in direction of the processor 16 causes the switch to activate the motor so as to rotate the processor 16 within a housing. A subsequent change in direction of the processor, as in from left to right, will activate the switch, causing the processor 16 to rotate 90 degrees from its existing position.

As illustrated in FIG. 3, a cutting block 30, having a convex configuration, may be utilized as a cutting surface when the donor tissue 12 is removed prior to processing, as may be done with a dermatome 14, and as previously illustrated in FIG. 1. The cutting block allows for even distribution of pressure by the processor 16 across the surface of the donor tissue 12 in order to ensure that the processed tissue particles are of uniform depth. Such uniformity has been shown to improve the cosmesis of the recipient site after the donor tissue 12 has established itself therein. In use, the processor 16 is rocked across the donor tissue 12, which is supported by the block 30, such that only a portion of the blades 18 are in contact with the donor tissue 12. The processor 16 is rocked across the donor tissue 12 such that an even distribution of cutting pressure is exerted across the surface of the donor tissue 12.

Figure 4B:
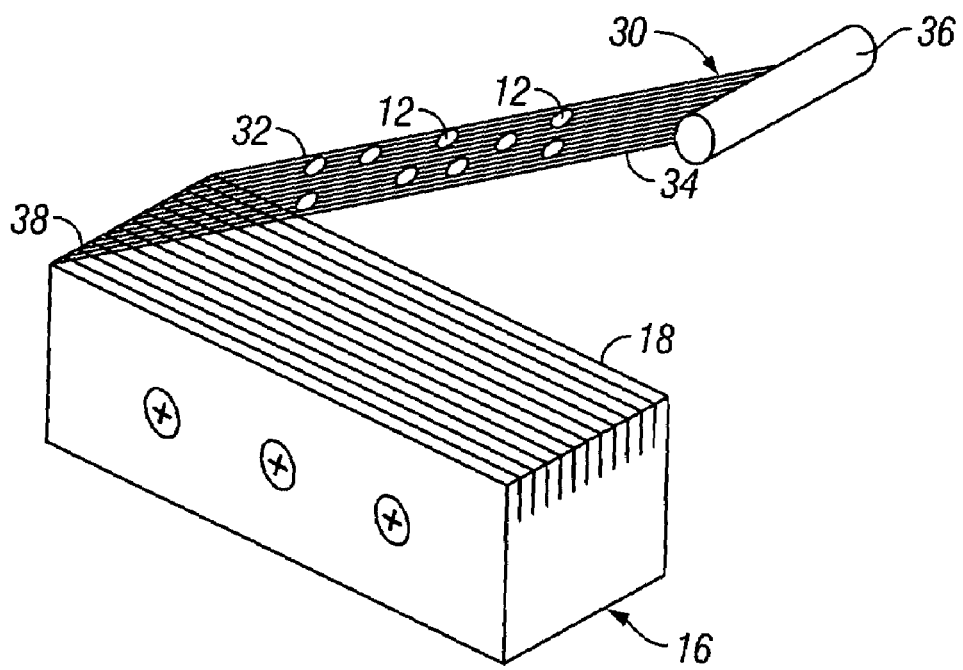

Turing now to FIGS. 4A and 4B, there is illustrated a tissue extractor 30 for removing the processed tissue 12 after it has been processed by the tissue processor 16 into the appropriate size. The tissue extractor 30 allows for the processed tissue 12 to be easily removed from the blades 18 of the processor 16. In a typical application, the small size of the processed tissue 12 may cause it to be trapped between the blades 18 of the processor, and cause difficulty in retrieving for subsequent placement at the donor site. The tissue extractor 30 consists of a series of strands 32 arranged in parallel, and secured at a distal end 34 to a handle 36. The proximal end 38 of the strands 32 may be secured to the processor, such that as the extractor 30 is pulled through the blades 18, the proximal end 38 of the strands 32 remain secured to the processor 16. The strands 32 are arranged such that each individual strand 32 occupies the spaced between each blade 18, and are positioned below the cutting surface of the blades 18 during application of the processor to the donor tissue 12. After processing of the tissue 12, the extractor 30 is pulled upward from its handle 36. In this process, the processed tissue 12 is captured by the strands 32 of the extractor 30, creating a screen for pulling the processed tissue 12 away from the blades 18. The processed tissue 12 may then be wiped, washed or otherwise removed from the extractor 30 for placement on the recipient site.

While the above description contains many specifics, these should not be construed as limitations on the scope of the invention, but rather as exemplifications of one or another preferred embodiment thereof. Many other variations are possible, which would be obvious to one skilled in the art. According, the scope of the invention should be determined by the scope of the appended claims and their equivalents, and not just by the embodiments.

What is claimed is:

1. A tissue processing system comprising:
a processor for processing tissue into particles for transplantation;
a tissue extractor for extracting processed tissue from said processor; and
wherein said tissue extractor is coupled to said processor at an end of said tissue extractor.

2. The tissue processing system of claim 1 further comprising a slicer for removing a tissue sample from a donor site.

3. The tissue processing system of claim 1 wherein said processor is further comprised of a plurality of blades in parallel arrangement.

4. The tissue processing system of claim 3 wherein said blades are adjustably secured so as to create a space between said blades.

5. The tissue processing system of claim 4 wherein said space is selectable from the set of about 250 microns, about 500 microns, and 1000 microns.

6. The tissue processing system of claim 4 wherein said space is adjustable within the range of about 250 microns through about 1000 microns.

7. The tissue processing system of claim 3 wherein said blades are fixedly positioned so as to create a space between said blades.

8. The tissue processing system of claim 7 wherein said space is about 250 microns.

9. The tissue processing system of claim 7 wherein said space is about 500 microns.

10. The tissue processing system of claim 7 wherein said space is about 1000 microns.

11. The tissue processing system of claim 3 wherein said tissue extractor is comprised of a plurality of strands positioned between said blades.

12. The tissue processing system of claim 11 wherein said strands are secured to proximal end of said processor.

13. The tissue processing system of claim 11 wherein said strands are secured to at least one end to form a handle for lifting said strands out of said processor.

14. The tissue processing system of claim 1 further comprising a cutting block for supporting said tissue during processing by said processor.

15. A tissue processing system, comprising:
a plurality of blades arranged in parallel and secured within a housing;
a tissus extractor connected to said housing at an end of said tissue extractor; and
a means for rotating said blades within said housing.

16. The tissue processing system of claim 15 wherein means for rotating said blades is comprised of an electric motor.

17. The tissue processing system of claim 16 further comprising a switch for activating said motor.

18. The tissue processing system of claim 17 wherein said switch is activated by a change in direction of said processor.

19. The tissue processing system of claim 15 wherein said means of rotating said blades rotates said blades 90 degrees.

* * * * *

UNITED STATES PATENT AND TRADEMARK OFFICE
CERTIFICATE OF CORRECTION

| | | |
|---|---|---|
| PATENT NO. | : 7,651,507 B2 | Page 1 of 1 |
| APPLICATION NO. | : 10/379342 | |
| DATED | : January 26, 2010 | |
| INVENTOR(S) | : Mishra et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 867 days.

Signed and Sealed this
Fourth Day of January, 2011

David J. Kappos
*Director of the United States Patent and Trademark Office*